US009561141B1

(12) United States Patent
Alvine et al.

(10) Patent No.: US 9,561,141 B1
(45) Date of Patent: Feb. 7, 2017

(54) ORTHOPEDIC CAST REMOVAL APPARATUS AND METHOD

(71) Applicants: Greg Alvine, Sioux Falls, SD (US); Matthew V. Leyden, St. Paul, MN (US); Nathan Schlueter, Bloomington, MN (US)

(72) Inventors: Greg Alvine, Sioux Falls, SD (US); Matthew V. Leyden, St. Paul, MN (US); Nathan Schlueter, Bloomington, MN (US)

(73) Assignee: Greg Alvine, Sioux Falls, SD (US)

( * ) Notice: Subject to any disclaimer, the term of this patent is extended or adjusted under 35 U.S.C. 154(b) by 267 days.

(21) Appl. No.: 14/208,676

(22) Filed: Mar. 13, 2014

Related U.S. Application Data

(60) Provisional application No. 61/779,280, filed on Mar. 13, 2013.

(51) Int. Cl.
| | | |
|---|---|---|
| *A61F 15/02* | (2006.01) | |
| *B26B 7/00* | (2006.01) | |
| *B26D 7/08* | (2006.01) | |
| *A61B 17/32* | (2006.01) | |

(52) U.S. Cl.
CPC ............... *A61F 15/02* (2013.01); *B26B 7/00* (2013.01); *B26B 7/005* (2013.01); *B26D 7/086* (2013.01); *A61B 17/320068* (2013.01); *A61B 2017/320072* (2013.01)

(58) Field of Classification Search
CPC .............. A61F 15/02; B26D 7/086; A61B 17/320068; A61B 2017/320072; B26B 7/00; B26B 7/005
See application file for complete search history.

(56) References Cited

U.S. PATENT DOCUMENTS

| | | | | |
|---|---|---|---|---|
| 2,522,006 | A * | 9/1950 | Wilcox | A61F 15/02 29/DIG. 64 |
| 5,355,587 | A | 10/1994 | Takekawa | |
| 5,733,074 | A * | 3/1998 | Stock | B23B 37/00 408/129 |
| 6,558,394 | B2 * | 5/2003 | Lee | A61F 15/02 30/390 |
| 7,824,247 | B1 * | 11/2010 | Bar-Cohen | B23B 37/00 125/28 |

FOREIGN PATENT DOCUMENTS

| | | |
|---|---|---|
| JP | 6122859 | 1/1986 |
| JP | 04156843 | 5/1992 |

(Continued)

*Primary Examiner* — Andrew Yang
(74) *Attorney, Agent, or Firm* — Jeffrey A. Proehl; Woods Fuller Shultz & Smith P.C.

(57) ABSTRACT

An apparatus for cutting a portion of an immobilization cast to facilitate removal of the cast from a body part of a patient may comprise a handle structure for being held by the hand of a user, a cutting device extending from the handle for cutting the cast material, with the cutting device including a blade and a blade movement device configured to cause ultrasonic movement of the blade, and a shielding structure configured for at least partially positioning between the cast and a part of the patient's body part such that a portion of the shield extends between the blade and the body part to shield the body part from the blade.

11 Claims, 12 Drawing Sheets

(56) References Cited

FOREIGN PATENT DOCUMENTS

| | | |
|---|---|---|
| JP | 04156844 | 5/1992 |
| JP | 04156845 | 5/1992 |
| JP | 04156846 | 5/1992 |
| JP | 07256600 | 9/1995 |
| KR | 100706771 | 5/2007 |
| KR | 1020090118171 | 11/2009 |

* cited by examiner

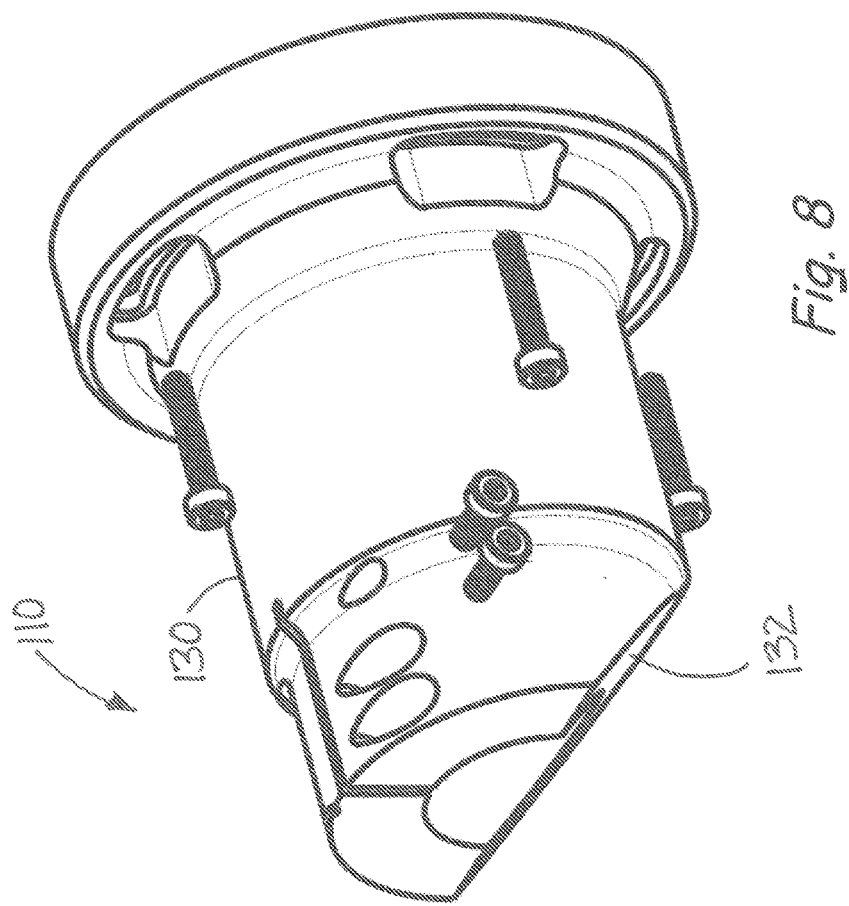
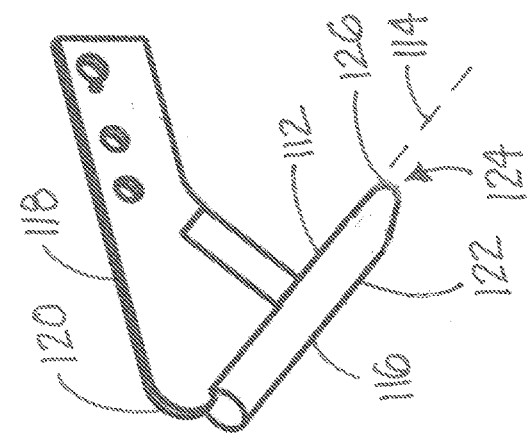
Fig. 8

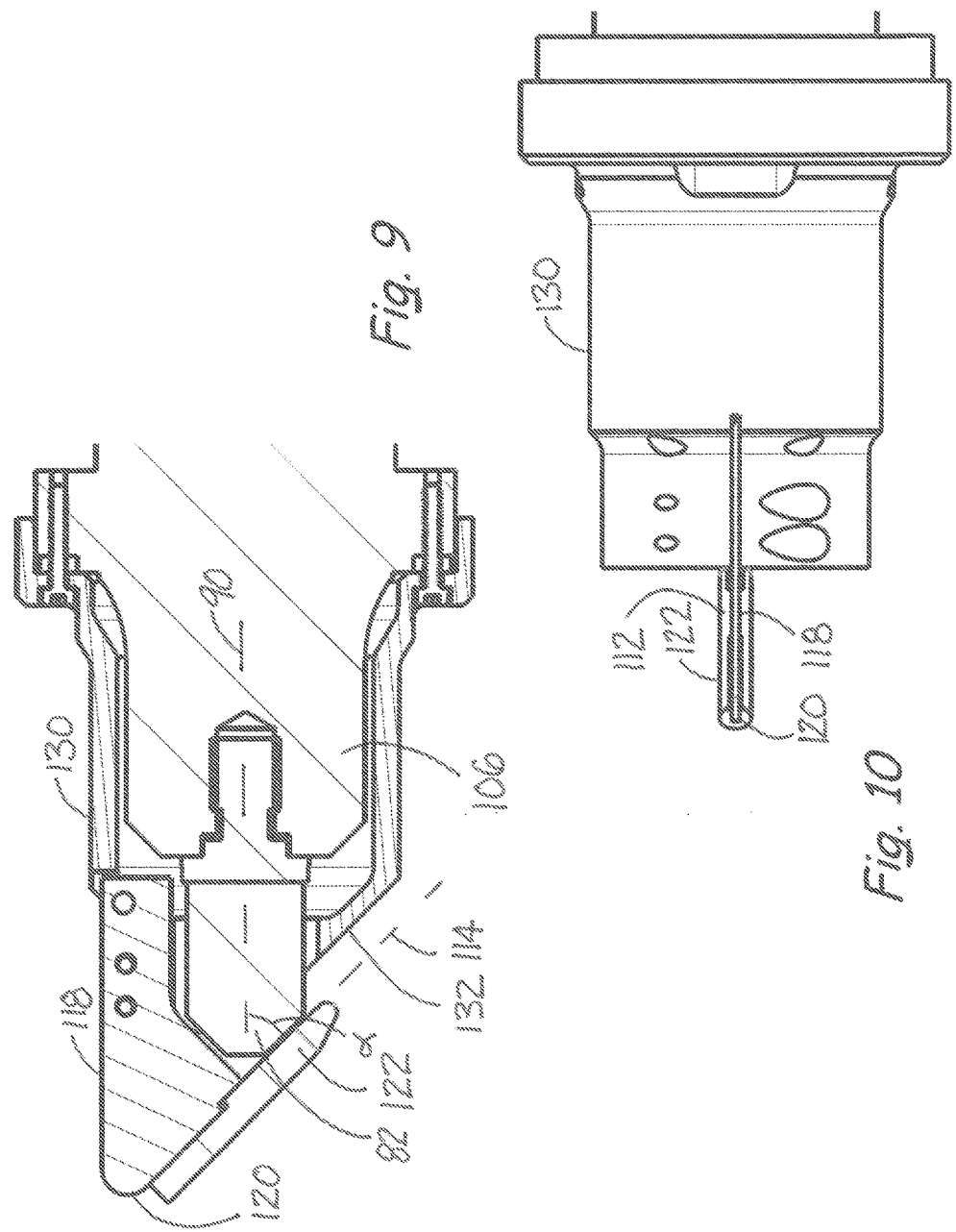

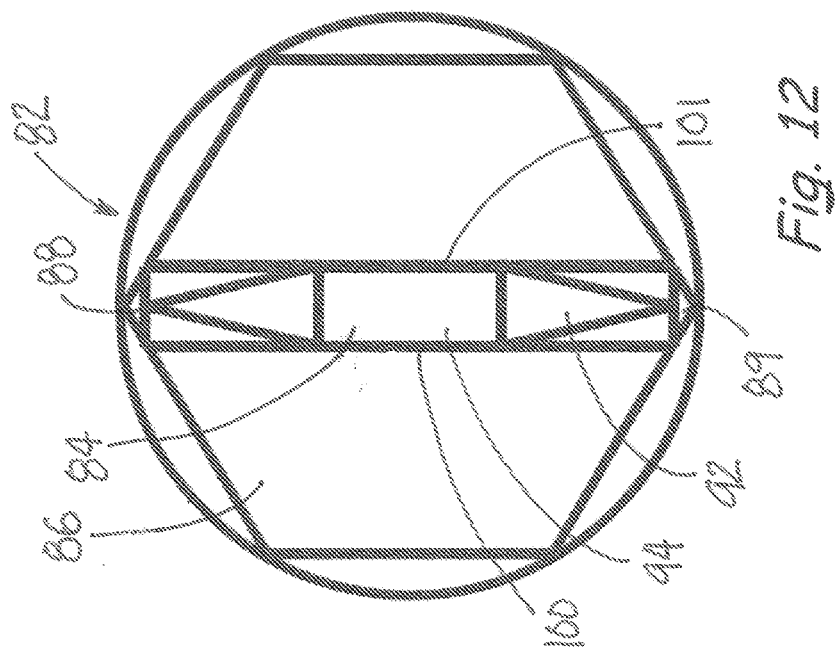
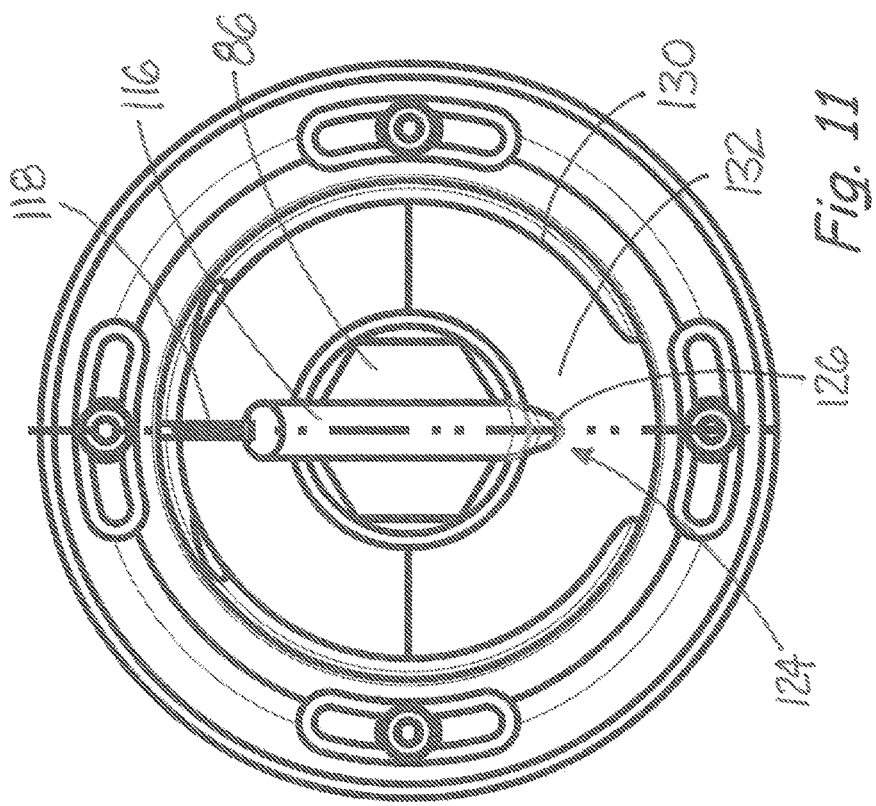

ORTHOPEDIC CAST REMOVAL APPARATUS AND METHOD

REFERENCE TO RELATED APPLICATIONS

This application claims the priority of U.S. Provisional Patent Application No. 61/779,280, filed Mar. 13, 2013, the disclosure of which is hereby incorporated by reference in its entirety.

BACKGROUND

Field

The present disclosure relates to orthopedic cast removal and more particularly pertains to a new orthopedic cast removal apparatus and method for providing a more comfortable and safer removal procedure.

Description of the Prior Art

Orthopedic casts are utilized to immobilize or substantially immobilize portions of the body of a patient. The cast is formed out of a rigid or substantially rigid material that encases the portion of the patient's body that is to be immobilized. Typically the cast is formed about the body part using a relatively flexible substrate that conforms to the body portion and a material that causes the substrate to become rigid so that the body part or parts are unable to freely move. For example, a flexible cotton mesh material may be rigidified by plaster of paris, or a flexible fiberglass mesh material may be rigidified by a resin. Once formed about the body part, the cast is worn on the body continuously for a period time to permit healing, and then the cast may be removed from the body part, typically by cutting or severing a portion of the cast, to permit release of the body part from the encasement by the cast.

SUMMARY

The present disclosure relates to an orthopedic cast removal apparatus that may include an insertion structure for inserting between the cast and the body part of the patient, may also include a shield structure positioned in a spaced arrangement with respect to the insertion structure, a handle structure for being held by the user, and a cutting device mounted on the insertion structure that is configured to cut the case material from a location inside the cast.

In one aspect, the disclosure relates to an apparatus for cutting a portion of an immobilization cast to facilitate removal of the cast from a body part of a patient. The apparatus may comprise a handle structure for being held by the hand of a user, a cutting device extending from the handle for cutting the cast material, with the cutting device including a blade and a blade movement device configured to cause ultrasonic movement of the blade, and a shielding structure configured for at least partially positioning between the cast and a part of the patient's body part such that a portion of the shield extends between the blade and the body part to shield the body part from the blade.

In another aspect, the disclosure is directed to an apparatus for cutting a portion of an immobilization cast to facilitate removal of the cast from a body part of a patient. The apparatus may comprise a handle structure configured for being held by the hand of a user, an insertion structure extending from the handle structure for positioning between a portion of the cast and a part of the patient's body part, with the insertion structure being elongated and having an outboard end and an inboard end. The outboard end may comprise a free end positionable between the body part and the portion of the cast. The apparatus may comprise a cutting device configured for cutting cast material, with the cutting device being mounted on the insertion structure for cutting the cast material from an inner surface of a wall of the cast. The cutting device may be located toward the outboard end of the insertion structure.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components, and particulars of the steps, set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein:

FIG. 8 is a schematic exploded perspective view of the shielding structure, according to an illustrative embodiment.

FIG. 9 is a schematic side sectional view of the cutting device and shielding structure of an illustrative embodiment of the cutting apparatus.

FIG. 10 is a schematic top view of a portion of the cutting apparatus.

FIG. 11 is a schematic front end view of the cutting apparatus according to an illustrative embodiment.

FIG. 12 is a schematic end view of an illustrative embodiment of the blade of the cutting device of an illustrative cutting apparatus.

DETAILED DESCRIPTION

The applicant has recognized that the use of conventional cast saws with oscillating blades has some significant drawbacks. One drawback is that a considerable amount of dust and cast material debris is created that may become airborne or otherwise may block the user's view of the cut being made in the cast material. As the cut is made from the outside to the inside of the cast wall, the blade moves toward the patient's skin, which the applicant has recognized makes it more difficult to avoid contact with the skin. Contact between the oscillating saw blade and the skin of the patient may cause a burn or a cut on the skin if the contact lasts for any duration that is less than momentary. Further, the applicant has recognized that considerable noise is made by the operation of the oscillating cutting saw, as well as by the blade's contact with the cast, which tends to cause unease in patients, especially children.

Applicant has developed an apparatus for cutting a cast with features that, used either alone or in combination with each other, alleviate disadvantages of conventional cast saws. Applicant has recognized that a cutting apparatus that utilizes ultrasonic vibrations creates less noise as well as dust and debris of conventional saws, and tends to alleviate the problems caused by these events. Furthermore, the applicant has developed embodiments of an apparatus that may initiate the ultrasonic cutting from a location that is between the patient's skin and an inner surface of the cast, rather than at a location at the outer surface of the cast, to help avoid contact with the skin of the body part as well as to alleviate some of the noise and dust creation. Applicant has also developed embodiments in which the blade of the cutting apparatus is positioned exterior to the cast, and includes shielding that protects the skin of the patient as well as guiding movement of the cutting apparatus with respect to the user's casted body part.

Figure 1:
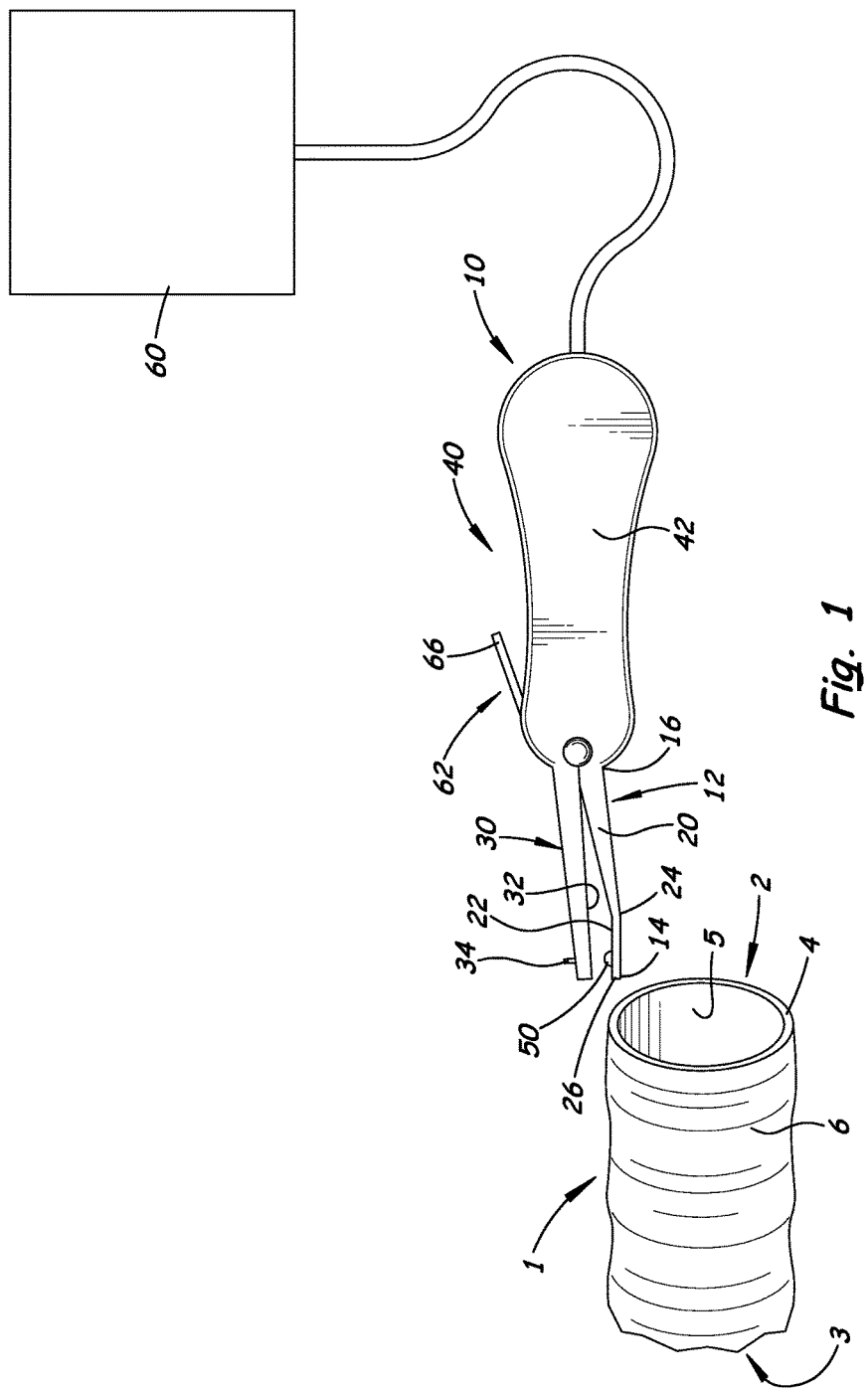
FIG. 1 is a schematic side view of an illustrative embodiment of a new orthopedic cast removal apparatus according to the present disclosure.
Figure 2:
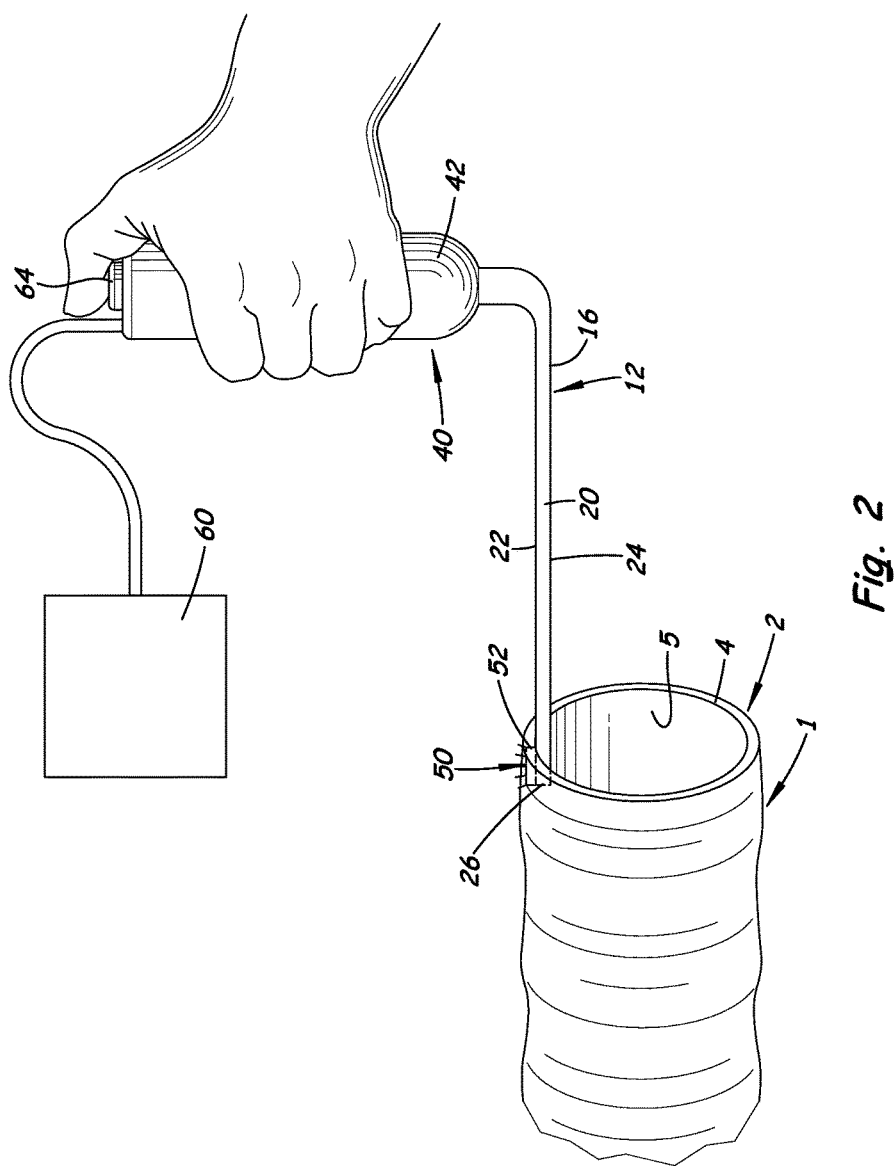
FIG. 2 is a schematic side view of another illustrative embodiment of the apparatus.
Figure 3:
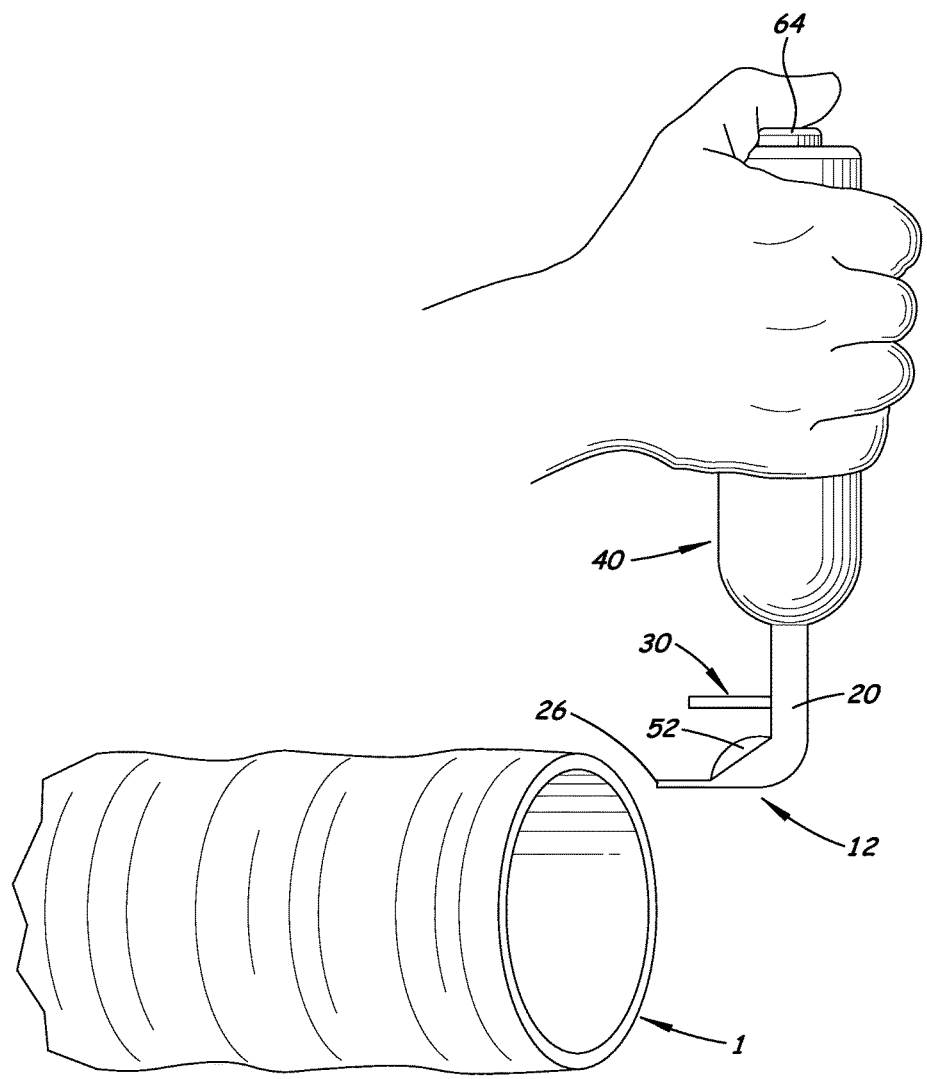
FIG. 3 is a schematic side view of the still another illustrative of the apparatus.
Figure 4:
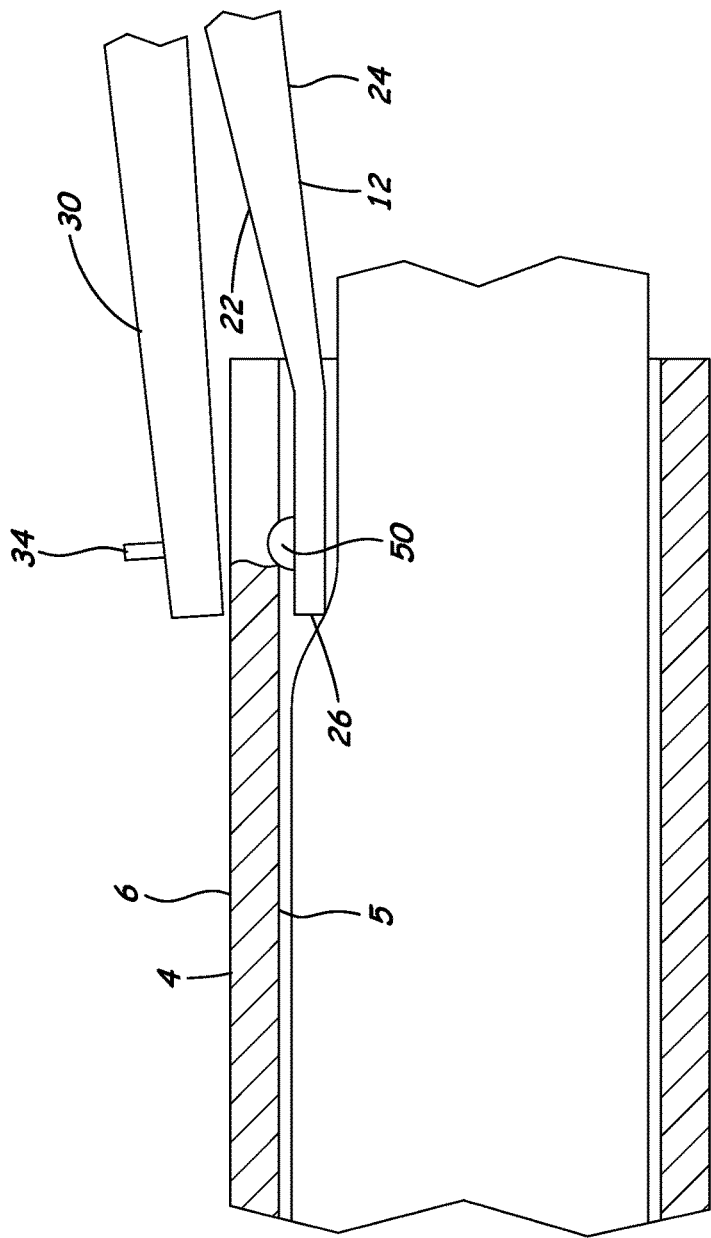
FIG. 4 is a schematic side sectional view of a cast in relation to a portion of an illustrative embodiment of the apparatus.
Figure 5:
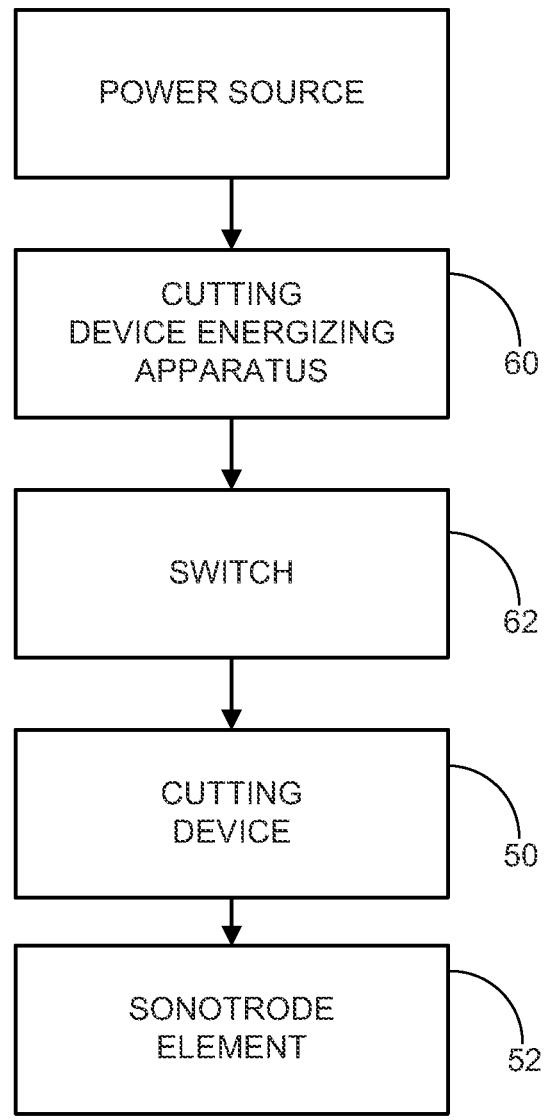
FIG. 5 is a schematic diagram of an embodiment of an illustrative embodiment of the apparatus.
Figure 6:
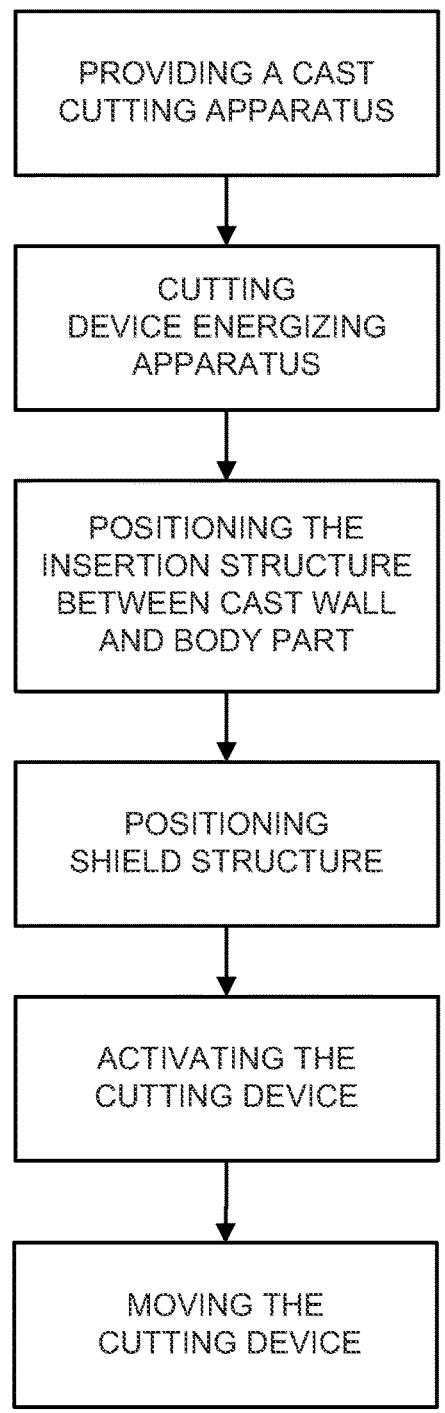
FIG. 6 is a schematic flow diagram on one illustrative implementation of a method according to the disclosure.
Figure 7:
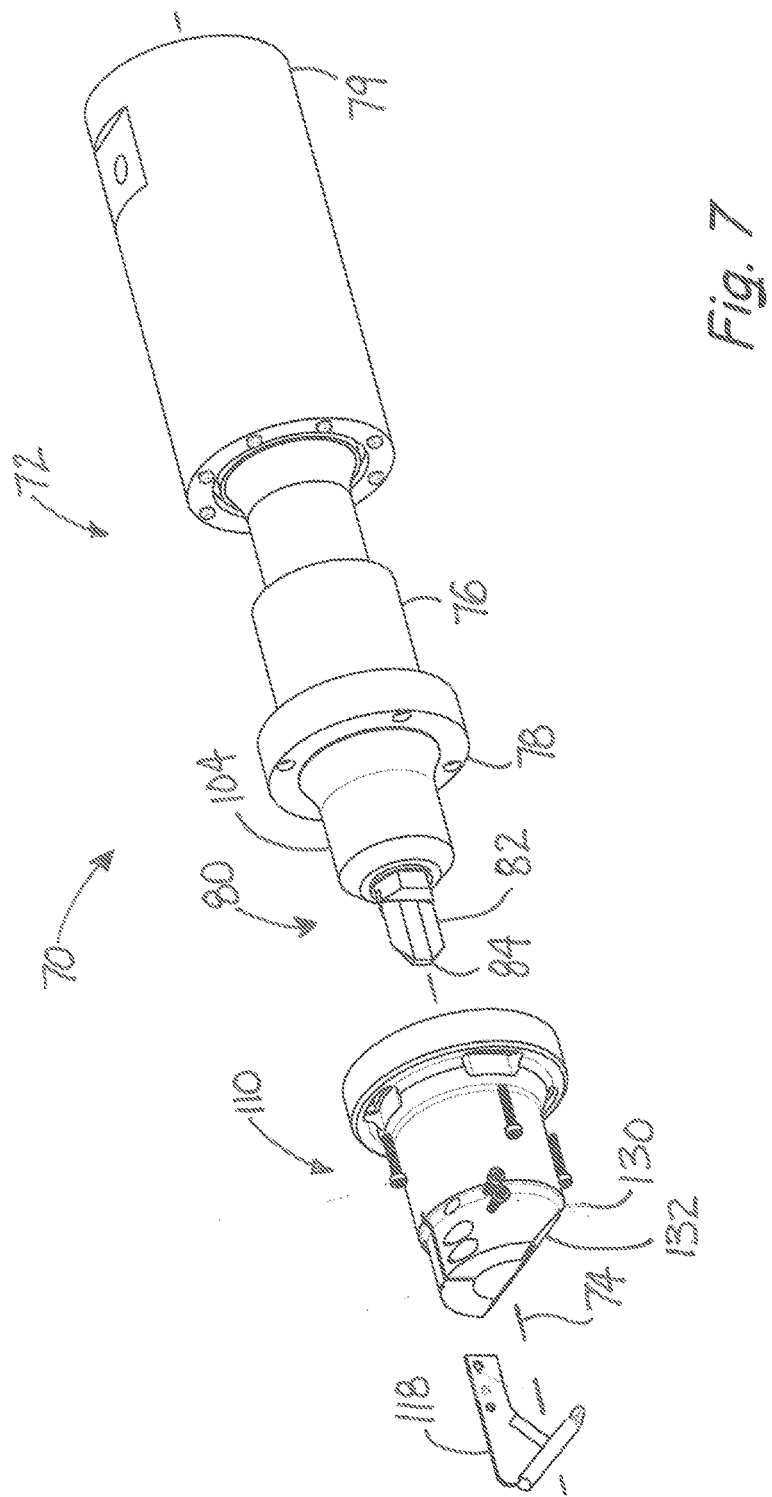
FIG. 7 is a schematic perspective view of an embodiment of the cutting apparatus in a partially exploded condition.
Figure 13:
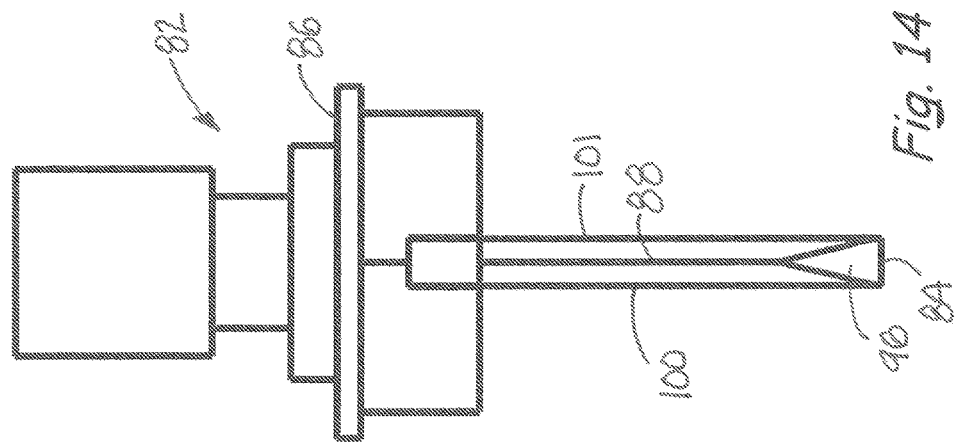
FIG. 13 is a schematic side view of the illustrative embodiment of the blade of the cutting device.
Figure 14:
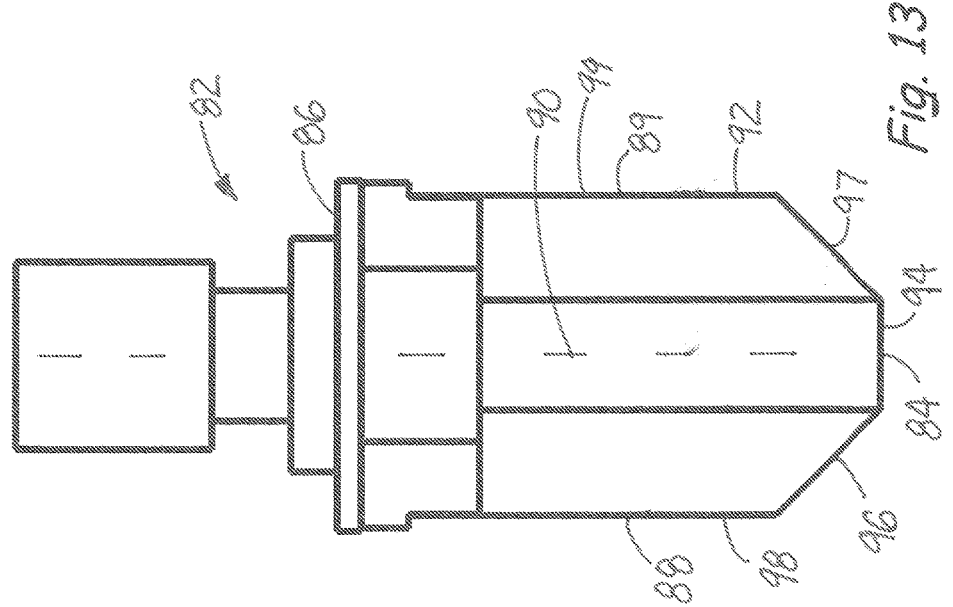
FIG. 14 is a schematic edge view of the illustrative embodiment of the blade of the cutting device.
Figure 15:
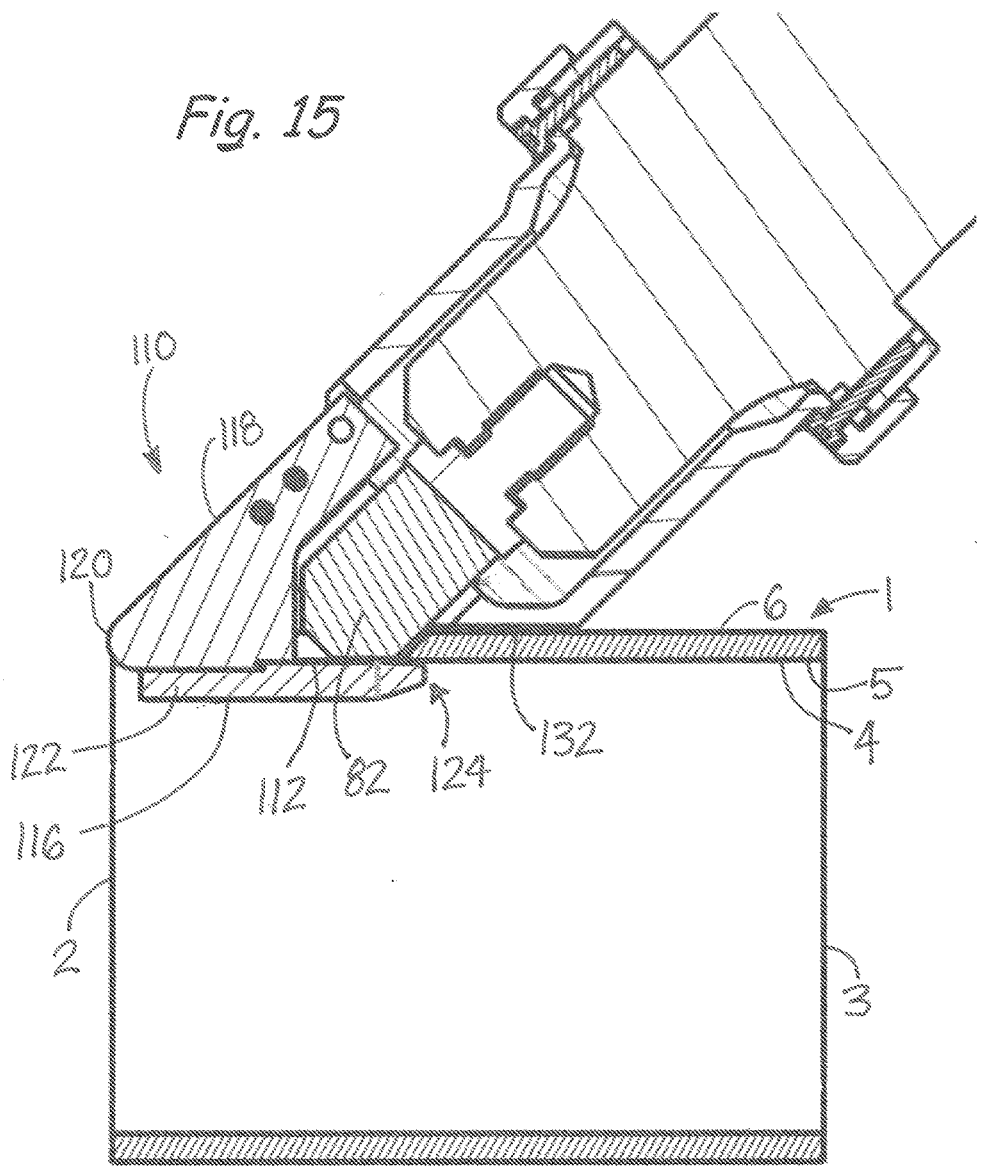
FIG. 15 is a schematic side sectional view of an illustrative embodiment of the cutting apparatus engaging a cast.

With reference now to the drawings, and in particular to FIGS. 1 through 15 thereof, a new orthopedic cast removal apparatus and method embodying the principles and concepts of the disclosed subject matter will be described.

Applicant has devised an apparatus 10 for cutting or severing a portion of an immobilizing cast 1 for facilitating the removal of the cast from a body part of a patient. The cast 1 typically has a first opening 2 for the body part to extend through, and may have a second opening 3 through which the same part or a different part of the body extends. The cast 1 has a cast wall 4 with an inner surface 5 positioned adjacent to the body part and may be in loose or snug contact with the skin on the body part. The cast wall 4 may also have an outer surface 6 that is positioned on an opposite side of the wall and is oriented away from the body part. Cutting the cast wall to release the body part from the cast generally involves forming a cut in the wall from one surface to the opposite surface of the wall.

In some embodiments, the apparatus 10 includes an insertion structure 12 that is configured for positioning between the cast 1 and the patient's body part. The insertion structure 12 may be adapted for insertion into a relatively small area or crevice, such as an area that may be formed between the inner surface 5 of the cast wall 4 and the part of the patient's body when the structure 12 is inserted. The insertion structure 12 may be being elongated along a longitudinal axis and may be relatively thin in character to facilitate movement in the confined area between the cast and body part. The insertion structure may have an outboard end 14 and an inboard end 16, with the outboard end being configured to be inserted between the body part and a portion of the cast 1 while the inboard end may remain outside of the cast. The insertion structure 12 may have a length of approximately 0.5 inches to approximately 12 inches between the outboard end 14 and the inboard end 16, and may have a length of approximately 1 inch to 6 inches, although other lengths may be utilized.

The insertion structure 12 in greater detail may comprise an arm portion 20 that has a first inward surface 22 and a first outward surface 22. The first inward surface 22 may be designed for orienting toward a portion of the cast 1 to be cut and the first outward surface 24 may be designed for orienting toward the body part of the patient, such as the skin. To this end the first outward surface may be relatively smooth and flat without significant variations or irregularities that might irritate the skin when moved across the skin. The arm portion 20 may terminate at a tip 26 that may be slightly pointed but generally not sharp, and the width of the arm portion may increase somewhat from the outboard end to the inboard end of the insertion structure to facilitate the ease of insertion between the skin and the cast. The arm portion 20 may be substantially rigid and formed of a material that provides the desired rigidity. The arm portion 20 may also be substantially straight between the inboard 16 and outboard 14 ends of the insertion structure.

The apparatus 10 may also include a shield structure 30 for positioning outwardly of the cast 1 in a spaced relationship to the insertion structure 12. The shield structure may generally provide a measure of protection from the dust and pieces of cast material liberated from the rest of the cast by the cutting action. The shield structure may have a second inward surface 32 positioned in opposition to the first inward surface 22 of the insertion structure, and may be positioned substantially parallel to the first inward surface 22. In some embodiments, at least a portion of the shield structure may have a width that is greater than the width of the insertion structure.

In some embodiments, the insertion structure 12 and the shield structure 30 may be movable with respect to each other. Illustratively, the movement may be pivot movement and the shield structure may be pivotally connected to the insertion structure to facilitate adjustable movement of the orientation of the structures 12, 30 with respect to each other.

The apparatus 10 may also have a handle structure 40 configured to be held or gripped by the hand of a user during use of the apparatus. The handle structure 40 may extend from the arm portion 20 of the insertion structure, and may also extend from the shield structure. In some embodiments, the handle structure 40 may extend along an axis that is oriented substantially parallel to a longitudinal axis of the insertion structure (see, e.g., FIG. 1), while in other embodiments the handle structure may extend along an axis that is oriented substantially perpendicular to the longitudinal axis of the insertion structure (see, e.g., FIGS. 2 and 3). The exterior surface 42 of the handle structure 40 may be contoured to enhance grippability by a hand, such as through the formation of alternating ridges and troughs.

The apparatus 10 further includes a cutting device 50 configured to cut the material of the cast material. The cutting device 50 may be mounted on the insertion structure 12 to initiate a cut from the inside of the cast to the outside of the cast, but also may be mounted on the shield structure to initiate a cut from the outside of the cast to the inside of the cast. In the illustrative embodiments, the cutting device is mounted on the insertion structure. The cutting device 50 may be located toward the outboard end 14 of the structure 12. Illustratively, the cutting device 50 may be located toward the tip 26 of the arm portion 30 on the first inward surface 22 of the arm portion for cutting cast material that is positioned outwardly of the arm portion. The cutting device may be oriented toward the shield structure if mounted on the insertion structure, or may be oriented toward the insertion structure if mounted on the shield structure.

In some of the most preferred embodiments, the cutting device 50 comprises a sonotrode element 52. The sonotrode element may include a plurality of transducers, which may be oriented in a stack, attached to the arm portion and being able to contact the inner surface 4 of the cast when the insertion structure is at least partially inserted between the cast material and the skin of the patient. For example, an alternating current oscillating at ultrasonic frequency may be applied to piezoelectric transducers to cause them to expand and contract. Illustratively, the frequency employed may range from approximately 20 kHz to approximately 70 kHz.

The shape and size of the sonotrode transducer utilized may be made suitable to make the quantity of vibratory energy applied to the cast material effective, as well as fit meet the size constraint of this application.

Additionally, the shield structure 30 may include a marking or other indicator 34 in general alignment with the cutting device to provide the user with an indication of the relative position of the cutting device on the inside of the cast when the insertion structure and the cutting device thereon are inserted into the cast and not otherwise viewable by the user.

The apparatus 10 may also include a cutting device energizing apparatus 60 that is configured to supply power to the cutting device 50, and may include a wave generator for supplying electrical power to the cutting device, such as the sonotrode. The energizing apparatus 60 may be connected to a primary electrical power source such as a wall electrical outlet, and may have additional controls for controlling the characteristics of the operation of the cutting device, such as operating frequency. In some embodiments, a blade is employed which is driven by an ultrasonic motor and an ultrasonic amplifier. The motor may produce a small amplitude, high frequency sinusoidal motion that may be greater than 20 kHz. The amplifier may amplify the amplitude of the motion produced by the motor such that the motion of the blade is more effective and useful. Te blade may be formed of a relatively hard metal material, although other materials may be employed.

A switch 62 may be configured to activate and deactivate operation of the cutting device 50, and may control the supply of power to the cutting device. The switch 62 may control power flow from the energizing apparatus 60 to the cutting device 50. In some embodiments, the switch 62 may be being mounted on the handle structure so as to be easily reachable and manipulatable by the fingers of a hand gripping the handle structure 40. In some embodiments, the switch may be actuated by a button 64 on the handle structure and extending from the exterior thereof, and in other embodiments the switch may be actuated by a trigger 66 extending from the handle structure. Power may be supplied to the cutting device by conductors, such as wires, that extend along the insertion structure.

Another aspect of the disclosure relates to a method of removing a body part immobilization cast 1 from a body part of a patient by cutting or severing a portion of the cast. The method may include providing an apparatus 10 having at least some of the elements described herein, and positioning the insertion structure of the apparatus between the cast 1 and the part of the patient's body that is at least partially surrounded by the cast. The outboard end 14 of the insertion structure may be inserted through the opening 3 of the cast 1 so that the cutting device, such as a sonotrode, is positioned and located adjacent to the inner surface 5 of the cast 1.

The method may further include a step of positioning the shield structure 30 adjacent to the outer surface 5 of the cast, when the apparatus 10 includes a shield structure, and may include positioning the shield in relative opposition to the insertion structure. The position of the shield structure may be adjusted to locate it relatively close to the outer surface 6, and may be adjusted to move the shield structure into a suitable position close to and in some cases in contact with the outer surface.

The method may further include activating the cutting device 50 such that the cutting device begins engaging the cast material and forming a cut in the material. The cutting device may be activated by actuating the switch or trigger on the handle structure or by another manner. In some embodiments, the actuation of the switch may cause the sonotrode to vibrate.

The method may also comprise moving the insertion structure 12 with respect to the cast 1 to thereby move the cutting device 50 along the inner surface 5 of the cast. In some techniques, the movement of the cutting device 50 may generally start at one opening 2 of the cast and away from the opening 2, and possibly toward another opening 3 of the cast. In other implementations, the movement of the cutting device may generally be toward the opening 2 of the cast, and may begin at a point on the cast spaced or separated from the opening. The movement of the insertion structure may thus at least partially be inside the cast.

The cutting device 50 may then be advanced or moved along the cast wall 4 toward or away from the cast opening to create a cut in the cast wall, and may be continued for a distance that allows the body part to be freed from the cast. In some implementations of the method, this may include moving the cutting device from one opening to the other to create a cut in the cast wall 4 from one opening to the other opening.

Another illustrative embodiment of the cutting apparatus 70 of the disclosure is shown in FIGS. 7 through 15, and may be characterized by cutting performed by a blade located primarily outside of the cast. The illustrative apparatus 70 may include a handle structure 72 for being held by the hand of the user, and may be elongated along a primary axis 74. The handle structure 72 may include a housing 76 which encloses various components of the apparatus, including, for example, a motor, an amplifier, power supply components, control components, and the like. The housing 76 has a forward end 78 and a rearward end 79. The motor may The cutting apparatus 70 may also include a cutting device 80 for engaging and cutting the cast material. The cutting device 80 may extend from the handle structure 72, and may extend from the forward end 78 of the housing 76. The cutting device 80 may include a blade 82 which may have a tip end 84 and a fixed end 86. The tip end of the blade may terminate in a tip, and the tip may be tapered in width. The blade has lateral sides 88, 89 that extend from the tip end 84 toward the fixed end 86, and a thickness of the blade may be tapered away from a central axis 90 of the blade toward the lateral sides 88, 89. The blade 82 may have a perimeter edge 92, and the perimeter edge may include a tip extent 94, a pair of side tip extents 96, 97 that extend on opposite sides of the tip extent, and side extents 98, 99 that are located on the lateral sides 88, 89 of the blade. The blade has opposite faces 100, 102, and the faces may converge at the perimeter edge 92 with the blade having a relatively thicker thickness at and along the central axis and tapering thinner toward the lateral sides. In general, while the blade has a relatively thin thickness along the perimeter edges to facilitate cutting of the case material, the middle of the blade may have a relatively thicker thickness to create a sufficiently wide cut to allow portions of the shielding structure to move through the cut after the blade has created, and then moved through, the cut.

The cutting device 80 may also include a blade movement device 104, and the blade may be mounted on the blade movement device in a manner such that the blade movement device is able to move the blade in a rapid manner to cause the cutting of the cast. The blade 82 may extend along the primary axis 74 from the blade movement device 104. The blade movement device 104 may further include a body 106, and the body may extend forwardly from the housing. The body 106 may be attached or otherwise in communication with the aforementioned motor and amplifier (if used).

The apparatus 70 may also include a shielding structure 110 for at least partially positioning between the cast wall 4 and a part of the patient's body. The shielding structure 110 may have a shield inward surface 112 which may be positioned in opposition to the blade of the cutting device and may be positioned adjacent to the blade 82. The shield inward surface 112 may be positioned adjacent to the tip end 84 of the blade, and may be in close proximity to the blade tip. The shield inward surface 112 may be in an inward surface plane 114, and the inward surface plane 114 may be oriented at an angle α with respect to the central axis 90 of the blade. The shielding structure 110 may have a width greater than a width of the blade 82. The shielding structure 110 may have a shield outward surface 116 for positioning adjacent to the body part during cast cutting or severing.

The shielding structure 110 may further include a support 118, which may extend along a portion of the blade 82. The support 118 may extend along a first one 96 of the side tip extent of the perimeter edge of the blade. The support 118 should be held relatively stationary with respect to the movement of the blade 82 during operation of the blade for cutting, and thus the support should be mounted on a part of the apparatus 70 that maintains the substantially moving condition of the support. The support 118 may extend from the housing 76 of the handle structure 72, and the support may be mounted, for example, on the forward end 78 of the housing although mounting on another structure, such as another location on the housing 76, may be employed. The degree or extent of extension of the support 118 may be adjustable, for example, to adjust to different cast wall thicknesses, blade lengths, etc. At least a portion of the support 118 should be relatively thin, and preferably thinner than the cut formed by the blade such that the portion of the support is able to move through the cut in the cast wall formed by the blade. The support 118 may have an outboard end 120, and the outboard end may be pointed.

The shielding structure 110 may also include a shield 122 that forms the shield inward surface 112 and the shield outward surface 116. The shield 122 may be mounted on the support 118, and may extend along a portion of the outboard end 120 of the support and may further extend from the outboard end of the support back toward the blade. The shield 122 may extend as a finger to a free end 124. The free end 124 may extend past the blade 82 and may form a tip 126. The shield inward surface 112 may extend along a second one 97 of the side tip extents of the perimeter edge of the blade. Optionally, the shield inward surface 112 may form a groove or slit that extends substantially parallel to the major plane of the blade. A portion of the tip end 84 of the blade may extend into the groove so that the gap between the tip end and the shield is partially or completely positioned in the groove (and the gap with the inward surface plane is essentially negative).

The shielding structure 110 may include a mount 130, and the support 118 may extend from the mount. The mount 130 may be mounted on the body 106 of the cutting device 80, and may enclose a portion of the cutting device. The mount 130 may enclose a portion of the blade movement device 104. The mount 130 may have a guide surface 132 for resting against an outer surface 6 of the cast wall of a cast being cut. The guide surface 132 in combination with the shield inward surface 112 may effectively provide opposite sides of a channel through which a portion of the cast wall is guided as the cutting apparatus is engaging and cutting the cast wall (see, e.g. FIG. 15)

It should be appreciated that in the foregoing description and appended claims, that the terms "substantially" and "approximately," when used to modify another term, mean "for the most part" or "being largely but not wholly or completely that which is specified" by the modified term.

It should also be appreciated from the foregoing description that, except when mutually exclusive, the features of the various embodiments described herein may be combined with features of other embodiments as desired while remaining within the intended scope of the disclosure.

Further, those skilled in the art will appreciate that the steps shown in the drawing figures may be altered in a variety of ways. For example, the order of the steps may be rearranged, substeps may be performed in parallel, shown steps may be omitted, or other steps may be included, etc.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

We claim:

1. An apparatus for cutting a portion of an immobilization cast to facilitate removal of the cast from a body part of a patient, the apparatus comprising:

a handle structure for being held by the hand of a user;

an ultrasonic cutting device extending from the handle for cutting the cast material, the cutting device including a blade and an ultrasonic blade movement device configured to cause ultrasonic cutting movement of the blade without causing rotation of the blade; and a shielding structure configured for at least partially positioning between the cast and a part of the patient's body part such that a portion of the shield extends between the blade and the body part to shield the body part from the ultrasonic cutting movement of the blade.

2. The apparatus of claim 1 wherein the shielding structure has a shield outward surface for positioning adjacent to the patient's body part, the shielding structure having a shield inward surface positioned in opposition to a tip end of the blade of the cutting device to shield the tip end of the blade from the patient's body part.

3. The apparatus of claim 1 wherein the shielding structure includes a mount having a guide surface for resting against an outer surface of the cast.

4. The apparatus of claim 3 wherein the shielding structure has a shield inward surface positioned in opposition to a tip end of the blade of the cutting device, and the guide surface of the mount and the shield inward surface of the shielding structure form opposite sides of a channel through which a portion of the cast is able to be guided as the blade engages the cast.

5. The apparatus of claim 1 wherein the shielding structure has a shield inward surface positioned in opposition to a tip end of the blade of the cutting device, the shield inward surface being positioned in an inward surface plane, the inward surface plane being oriented at an angle with respect to a central axis of the blade.

6. The apparatus of claim 1 wherein the shielding structure comprises a support extending along a portion of the blade; and a shield mounted on the support and extending along a portion of an outboard end of the support, the shield extending from the outboard end of the support back toward the blade such that the support and shield surround a portion of a perimeter of the blade.

7. The apparatus of claim 6 wherein the shield extends as a finger to a free end, the free end extending past the perimeter of the blade.

8. An apparatus for cutting a portion of an immobilization cast to facilitate removal of the cast from a body part of a patient, the apparatus comprising:

a handle structure configured for being held by the hand of a user;

an insertion structure extending from the handle structure for positioning between a portion of the cast and a part of the patient's body part, the insertion structure being elongated and having an outboard end and an inboard end, the outboard end comprising a free end positionable between the body part and the portion of the cast; and an ultrasonic cutting device configured for cutting cast material, the cutting device being mounted on the insertion structure for cutting the cast material from an inner surface of a wall of the cast, the cutting device being located toward the outboard end of the insertion structure, the cutting device including a blade and an ultrasonic blade movement device configured to cause ultrasonic cutting movement of the blade without causing rotation of the blade.

9. The apparatus of claim 8 additionally comprising a shield structure extending in a spaced relationship to the insertion structure for positioning outwardly of the cast when the insertion structure is at least partially inserted into the cast, the cutting device being directed toward the shield structure.

10. The apparatus of claim 9 wherein the insertion structure and the shield structure are movable with respect to each other.

11. The apparatus of claim 10 wherein the insertion structure and the shield structure are pivotable with respect to each other.

* * * * *